United States Patent [19]
Boris

[11] Patent Number: 5,259,840
[45] Date of Patent: Nov. 9, 1993

[54] LOCKING SYRINGE

[76] Inventor: Craig R. Boris, 7000 Government Way, Couer D'Alene, Id. 83814

[21] Appl. No.: 753,931

[22] Filed: Sep. 3, 1991

[51] Int. Cl.⁵ ............................................. A61M 5/00
[52] U.S. Cl. .................................... 604/110; 604/218; 604/220
[58] Field of Search ............... 604/110, 187, 192, 263, 604/218, 220

[56] References Cited

U.S. PATENT DOCUMENTS

| | | |
|---|---|---|
| 4,731,068 | 3/1988 | Hesse . |
| 4,820,272 | 4/1989 | Palmer . |
| 4,840,616 | 6/1989 | Banks ............................... 604/218 X |
| 4,846,796 | 7/1989 | Carrell et al. . |
| 4,909,795 | 3/1990 | Gelabert ........................ 604/110 X |
| 5,021,047 | 6/1991 | Movern ................................ 604/110 |
| 5,037,394 | 8/1991 | Mazurik et al. ..................... 604/110 |

FOREIGN PATENT DOCUMENTS

| | | |
|---|---|---|
| 2613628 | 10/1986 | France . |
| 8900432 | 1/1989 | PCT Int'l Appl. ................. 604/110 |
| 2197792 | 6/1988 | United Kingdom ................ 604/110 |

OTHER PUBLICATIONS

Two pages from the U.S. Patent and Trademark Office *Official Gazette*, Nov. 28, 1989, pp. 1826–1827 listing U.S. Pat. Nos. 4,883,471 and 4,883,470.
Two pages from the U.S. Patent and Trademark Office *Official Gazette*, Oct. 17, 1989, pp. 1308–1309 listing U.S. Pat. Nos. 4,874,385, 4,874,384, 4,874,383 and 4,874,382.
"Inventor of the Month Announced," Inventors Workshop International, Orange County Chapter Newsletter, Oct. 1990.

*Primary Examiner*—John D. Yasko
*Attorney, Agent, or Firm*—Knobbe, Martens, Olson & Bear

[57] ABSTRACT

A locking syringe is disclosed which comprises a plunger, a cylinder, and a cap. The plunger includes a proximal end and a distal end having a first set of annular ridges formed thereon. The cylinder comprises an open cylindrical passage and includes a needle attached in a conventional manner at the proximal end thereof. A plurality of annular ridges are formed inside the passageway at the distal end of the cylinder. The ridges in the cylinder engage the annular ridges on the plunger in a snap fit and prevent removal of the plunger from the cylinder after the syringe has been used. The cylinder also includes a plurality of annular ridges formed adjacent the needle. The ridges on the cylinder snap fit into mating annular ridges in the cap to prevent re-use of the needle once the syringe is discarded.

10 Claims, 6 Drawing Sheets

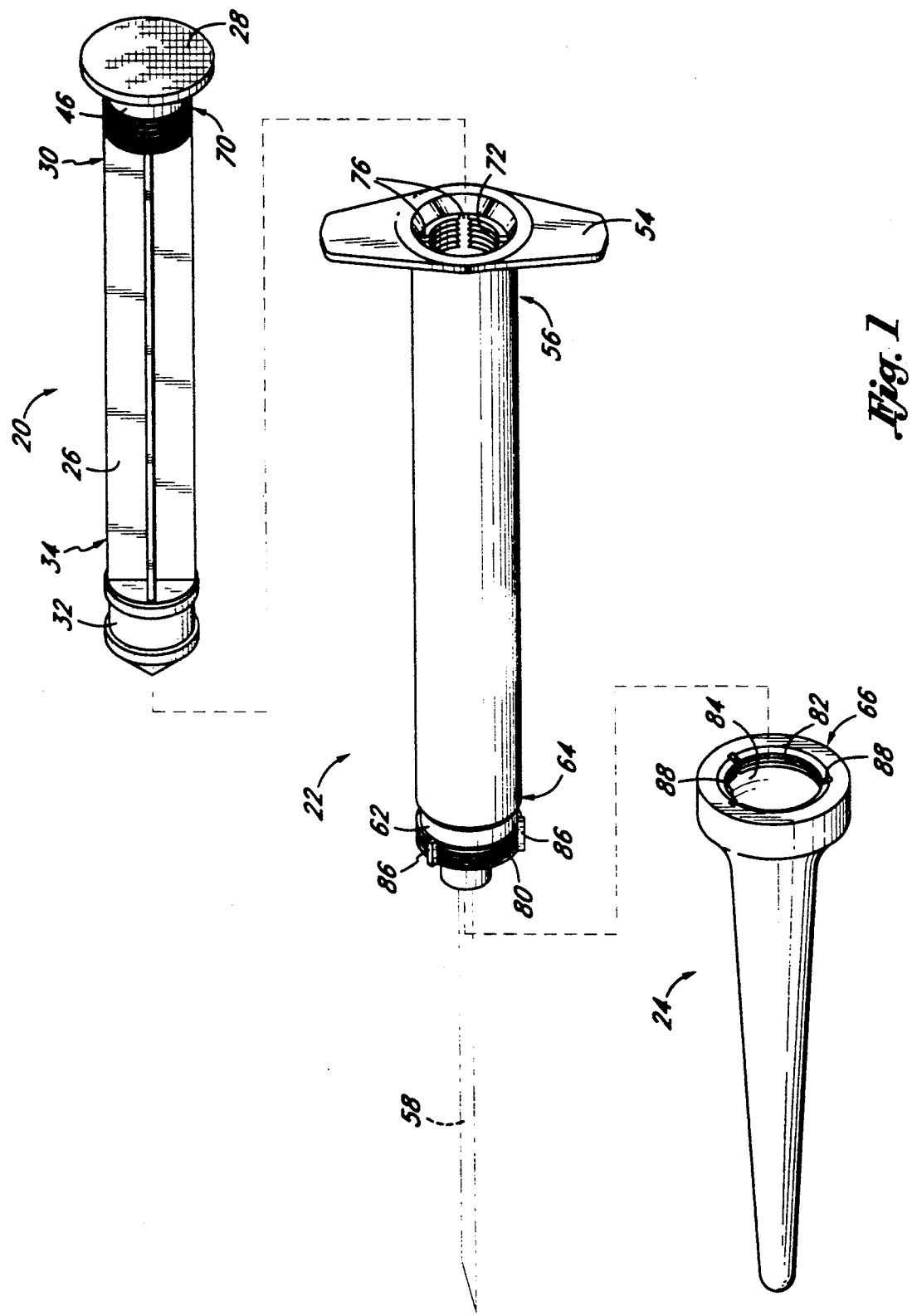

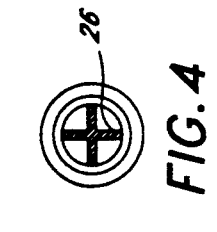
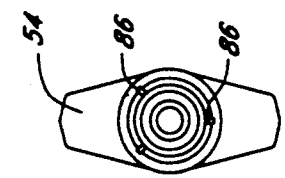
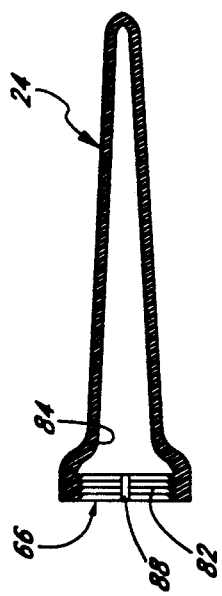
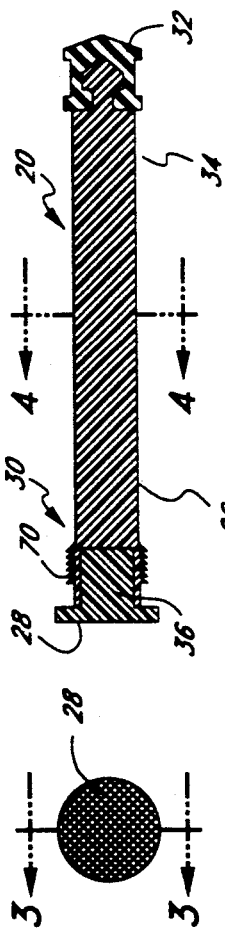
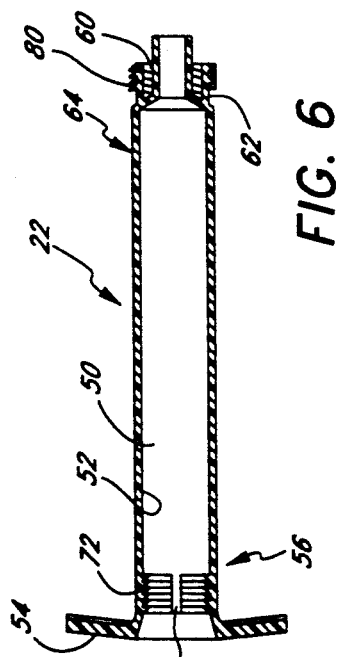
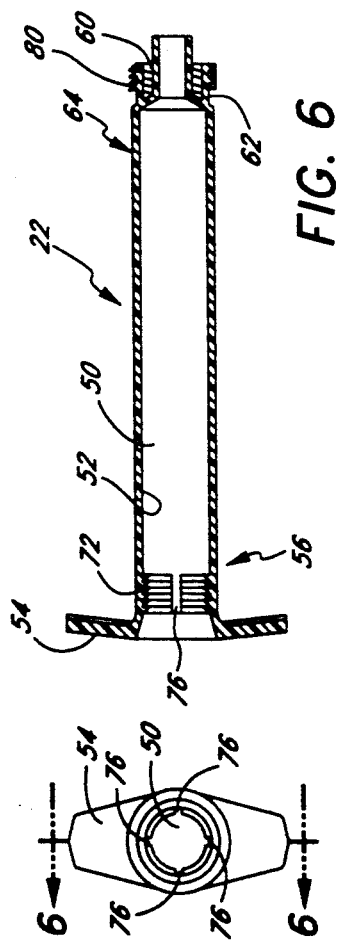
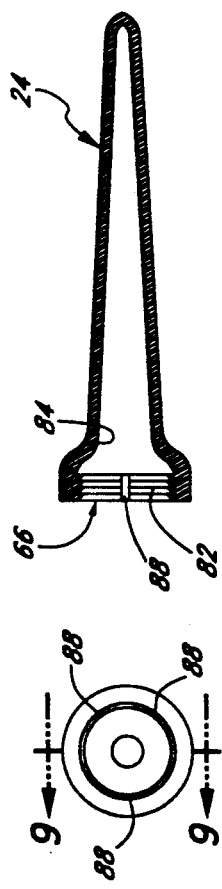

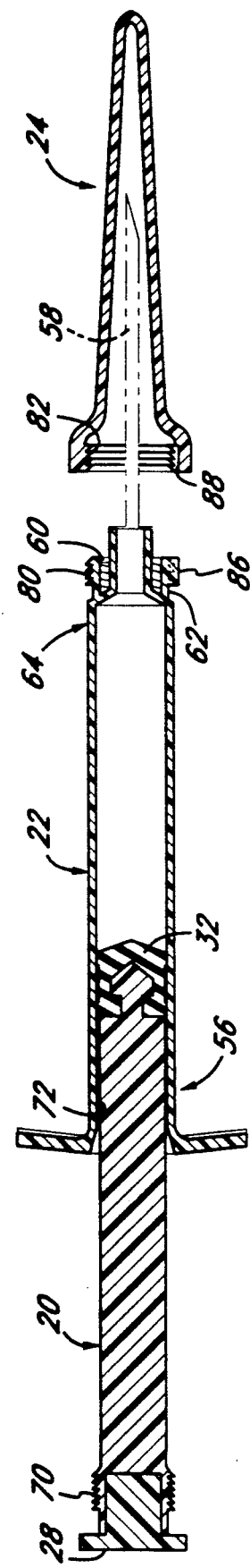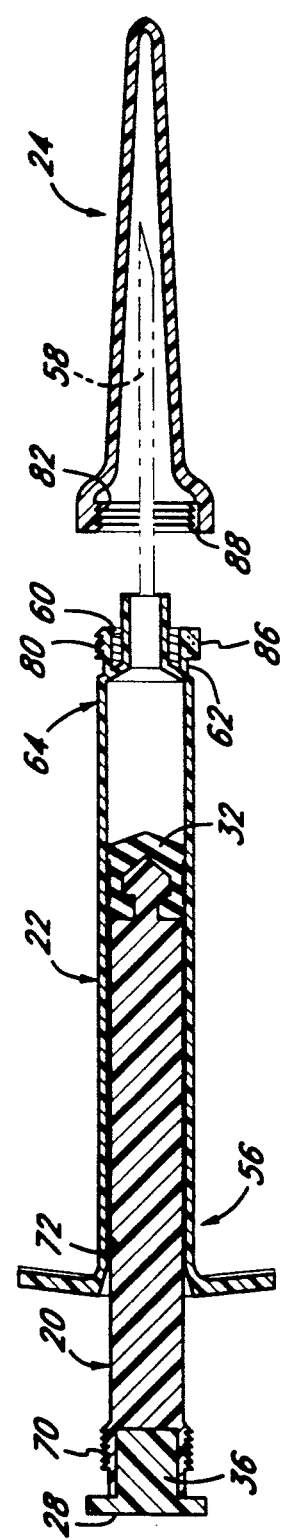

LOCKING SYRINGE

FIELD OF THE INVENTION

The invention relates to hypodermic syringes, and, in particular, to a syringe which can only be used once and which can be disposed of safely.

BACKGROUND OF THE INVENTION

Many serious and communicable diseases can be transmitted through the blood of an infected person. It is well known that viruses and bacteria are often carried in blood and can be passed on to others through contact with the contaminated blood. One such disease which can be spread by contact with a sample of blood carrying the virus is Acquired Immune Deficiency Syndrome, or AIDS, for which there is currently no cure. This disease has spread to significant proportions due to transmission of the virus through blood or other bodily fluids of infected persons.

Medical personnel are particularly susceptible to the spread of disease because of their frequent contact with the carriers of the disease. Syringes used to administer injections or remove bodily fluids for testing pose a substantial risk to doctors, nurses, and other medical personnel because of the chance of contact with the blood or bodily fluid and the possibility that the disease may enter the bloodstream of the medical technician through an exposed cut or abrasion or an accidental needle prick. Sanitation workers are also susceptible to accidental needle contact which can result in exposure to bacteria and viruses. For this reason, it is desirable that hypodermic syringes used to administer injections or extract bodily fluids for analysis and testing comprise a safety system so as to minimize accidental contact with the hypodermic needle and patient blood carried thereon.

In addition to inadvertent contact with infected blood, the spread of highly communicable diseases such as AIDS can be effected by re-use of the hypodermic needles and syringes described above. The needles are often sought by drug addicts to inject drugs intravenously into the blood stream. When used by drug addicts, the needles are often unclean and unsterilized, and thus, any virus or bacteria contained within residual blood or body fluids from the previous user is readily transmitted to the drug addict. The needles are often shared by the drug users, resulting in further spread of any bacteria or viruses contained in bodily fluids carried on the needles. Therefore, it is desirable to dispose of the syringes in a manner which prohibits their reuse.

Several syringes have been designed with protective elements in an attempt to minimize inadvertent needle contact and prevent reuse of the needle. One such syringe is shown in FIG. 1 of U.S. Pat. No. 4,820,272 entitled "Non-Reusable Hypodermic Syringe". The syringe comprises a cylinder having a series of inwardly extending grooves formed near the top end and a plunger having a mating series of outwardly extending grooves formed at the bottom end. These grooves allow the full insertion of the plunger within the cylinder but impede its withdrawal. French patent publication 2613628 discloses a similar type of syringe having flexible teeth formed in a piston which engage teeth in an outer tubular body to allow movement of the piston in one direction only. U.S. Pat. No. 4,731,068 entitled "Non-Reloadable Syringe" also discloses a syringe including means to prohibit retraction of the plunger once the contents of the syringe have been discharged.

SUMMARY OF THE INVENTION

The present invention provides a syringe which prevents accidental needle contact by medical personnel while also ensuring that the syringe cannot be used again after it has been disposed. The syringe includes a plunger which slides within an open, cylindrical passage in a cylinder. A needle is positioned on the end of the cylinder and discharges liquid through an opening as the plunger forces the liquid to the bottom of the cylinder. A plurality of annular grooves are formed in the inside wall of the cylinder, adjacent the end opposite the needle end of the cylinder. The grooves engage corresponding annular ridges formed adjacent the top of the plunger when the plunger is inserted in the syringe cylinder, preventing withdrawal of the plunger from the cylinder. A cap is provided to cover the needle after the syringe has been used. The cap is tapered in shape, having a wide opening at the end which connects to the cylinder so as to minimize the risk of contact with the needle when the cap is positioned on the cylinder. The cap includes a plurality of annular ridges which snap fit over corresponding annular grooves formed on the exterior of the syringe cylinder. The snap fit acts to prevent removal of the cap once positioned on the cylinder, thus providing further safety against re-use of the syringe. The locking cap also ensures that the cap is not disengaged after use of the syringe, thereby minimizing accidental needle contact. By prohibiting re-use and accidental needle contact, the syringe further provides assurance and security to persons receiving injections. A cap holder may further be provided for facilitating attachment of the cap to the cylinder.

BRIEF DESCRIPTION OF THE DRAWINGS

FIG. 1 is an exploded perspective view of a locking syringe and cap in accordance with the present invention;

FIG. 2 is an end view of the distal end of the plunger;

FIG. 3 is a side cross-sectional view of the plunger taken along lines 3—3 of FIG. 2;

FIG. 4 is a cross-sectional view of the plunger taken along lines 4—4 of FIG. 3;

FIG. 5 is an end view of the distal end of the cylinder;

FIG. 6 is a side cross-sectional view of the syringe cylinder taken along lines 6—6 of FIG. 5;

FIG. 7 is an end view of the proximal end of the cylinder;

FIG. 8 is an end view of the mouth of the cap;

FIG. 9 is a side cross-sectional view of the syringe cap taken along lines 9—9 of FIG. 8;

FIGS. 10 and 11 are cross-sectional views of the syringe illustrating the injection process;

DETAILED DESCRIPTION OF THE INVENTION

Figure 12:
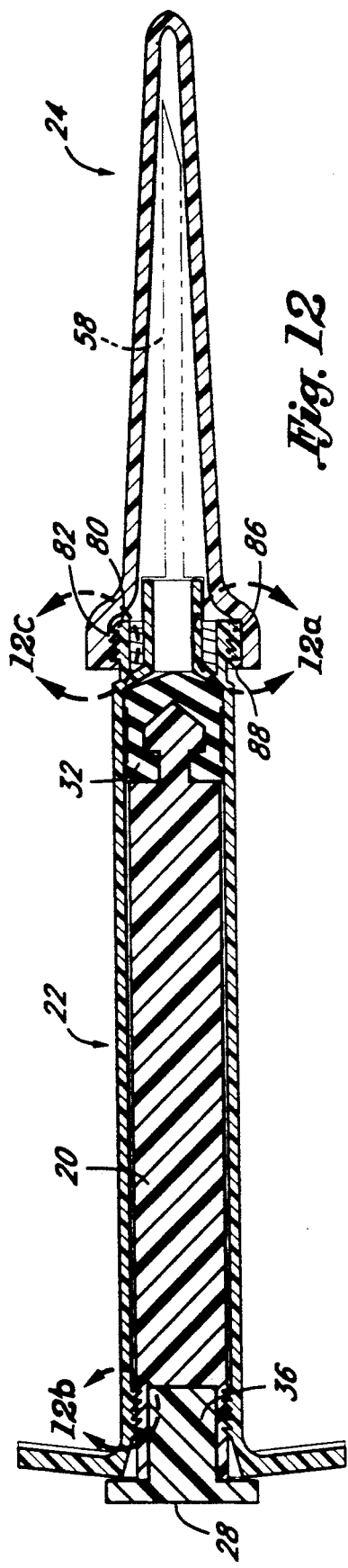
FIGS. 12, 12a, 12b, and 12c are assembled cross-sectional views of the syringe.
Figure 12C:
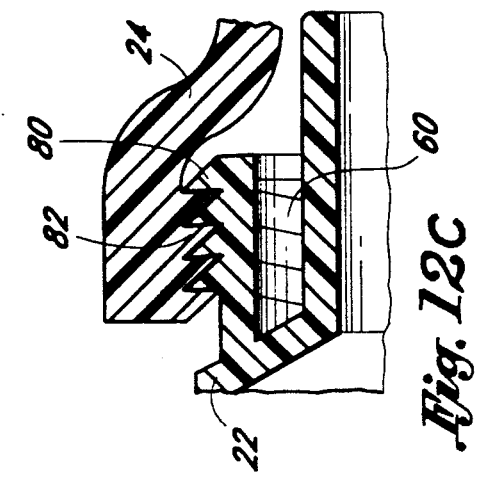

Referring to the Figures wherein like features are numbered identically throughout, the locking syringe of the present invention comprises a plunger 20, a housing or cylinder 22, and a cap 24. The plunger 20 is preferably a standard syringe plunger formed of Polystyrene or Polypropelene and comprises a shaft 26 having a cross-section which is a cruciform, i.e. "X" shaped, as best illustrated in FIG. 4. The plunger 20 is preferably formed of medical grade (Lexan having a 10% glass fill and includes a circular grip or thrust plate 28 located at a distal end 30 of the shaft 26. A rubber piston 32 is attached in a known manner to a proximal end 34 of the shaft 26, opposite the thrust plate 28. As best shown in FIG. 5, the thrust plate 28 is advantageously molded as a separate piece 36 which fits within the distal end 30 of the shaft 26 to form the plunger 20.

The cylinder 22 comprises an open, cylindrical passage 50 surrounded by an inner wall 52 and is also preferably formed of medical grade Lexan having a 10% glass fill. A grip or handle 54 is formed at a distal end 56 of the cylinder 22. A needle 58 (shown schematically) is conventionally engaged with a plurality of internal threads 60 formed inside a neck portion 62 at a proximal end 64 of the cylinder 22, opposite the grip 54. The syringe cap 24 is also preferably formed of medical grade Lexan having a 10% glass fill and comprises a wide opening or mouth 66 sized to cover the proximal end 64 of the cylinder 22, and tapers in width, having sufficient length and width to enclose the needle 58.

Figure 12B:
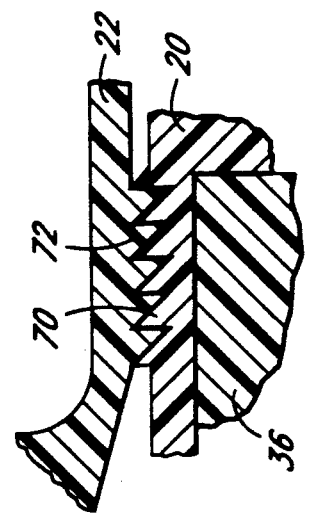
Figure 12A:
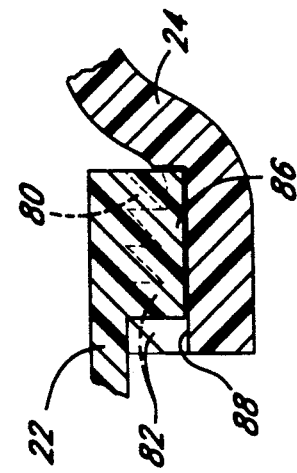

The syringe advantageously includes a plunger lock element to prevent re-use of the syringe once an injection has been given. Preferably, the plunger lock element comprises a first set of annular ridges 70 formed on the exterior surface of the shaft 26 proximate the thrust plate 28. The plunger lock element further comprises a second or mating set of annular ridges 72 formed along the inner wall 52 of the cylindrical passage 50 at the distal end 56 of the cylinder 22. It should be apparent to those skilled in the art, however, that other locking elements which create a snap, press, or other deformable locking fit could also be used. Four evenly-spaced channels 76 extend through the annular ridges 72 formed in the inner wall 52 to assist in accommodating the cruciform shaft 26 of the plunger 20 as it is inserted into the cylinder 22. In FIGS. 12 and 12b, the syringe is shown with the plunger 20 slightly twisted with respect to the cylinder 22 in order to better show the engagement of the locking elements 70, 72.

The syringe further includes a cap lock element which prevents re-use of the needle 58. Preferably, the cap lock element comprises a first set of annular ridges 80 formed on the exterior surface of the neck portion 62 of the cylinder 22. The ridges 80 mate with a second or mating set of annular ridges 82 formed in an inside wall 84 of the cap 24 adjacent the mouth 66. Again, those skilled in the art will recognize that other locking elements creating a snap, press, or other type of deformable locking fit could also be used. A plurality of raised surface structures 86 project outwardly from the ridges 80 on the neck 62. Preferably these surface structures 86 comprise three tabs, each having a longitudinal axis parallel to the longitudinal axis of the cylinder 22, which are spaced at unequal intervals around the ridges 80. As will be described in more detail below, the tabs 86 fit within corresponding slots 88 formed through the ridges 82 within the inside wall 84 of the cap 24 to lock the cap 24 onto the syringe cylinder 22.

FIGS. 10 and 11 illustrate the operation of the locking syringe. When an injection is given, the cruciform sections of the plunger 20 are aligned with the channels 76 formed within the ridges 72 along the inner wall 52 of the cylinder 22. The plunger 22 is then inserted within the cylindrical passage 50 and is free to move longitudinally within the cylinder 22, and back out to draw fluid into the cylinder 22 in a well-known manner. The ridges 72 forming part of the plunger lock element are advantageously formed at the distal end 56 of the cylinder 22 so as not to come in contact with the fluid drawn into the cylinder, thereby avoiding the possibility that the ridges 72 would permit the formation of air bubbles in the cylinder body as fluid is drawn into the syringe or otherwise adversely affect administration of an injection. After the desired amount of fluid has been drawn into the cylinder 22, the syringe is ready for the administration of an injection and the plunger 20 is again moved relative to the cylinder 22, using the thrust plate 28 and the handle 54. As the piston 32 carried on the plunger 20 travels the length of the passage 50, the liquid contained within the passage 50 is forced out through the needle 58.

As illustrated in FIG. 12, when all the liquid in the passage 50 has been ejected and the plunger 20 is completely inserted inside the cylinder 22, the annular ridges 70 on the plunger 20 engage and snap fit into the mating annular ridges 72 inside the wall 52 of the cylinder 22. As described above, the plunger 20 and cylinder 22 are preferably formed of medical grade Lexan, however, both sets of ridges 70, 72 could also be formed of other plastic materials which permit this snap fit. As is well known, a snap fit of this type requires that the material be somewhat flexible to permit the ridges 70, 72 to bend and then snap back to hold the plunger 20 and cylinder 22 longitudinally fixed with respect to one another. In this manner, removal of the plunger 20 from the cylinder 22 once the plunger 22 has been completely inserted within the cylinder is prevented, and the syringe cannot be used again.

Although it is not illustrated, the cruciform sections of the plunger could be slightly wider such that the outside edges thereof extend approximately even with or slightly beyond the outside edges of the ridge 70 such that when the plunger 20 is fully inserted within the cylinder 22, the plunger could only be removed by aligning the four edges of the cruciform-shaped shaft 26 with the four slots in the upper part 56 of the cylinder 22. Thus, a user could make it even more difficult to reuse the syringe by simply twisting the plunger 20 with respect to the cylinder 22 so that the four edges of the cruciform-shaped shaft 26 are not aligned with the four slots in the upper part 56 of the cylinder 22. Alternatively, the cruciform sections of the plunger 20 could extend through the annular ridges 70 on the plunger 22, like the tabs 86 on the exterior of the cylinder 22 at the needle end thereof. This would act to prevent twisting of the plunger 20 within the cylinder 22 after use and locking of the syringe, thus further deterring removal of the plunger 20 from the cylinder 22.

Before disposal of the syringe, the cap 24 is placed over the proximal end 64 of the cylinder 22 so as to cover and enclose the needle 58 carried thereon. The cap 24 is placed on the cylinder 22 such that the slots 88 in the interior wall 84 of the cap 24 are aligned with the tabs 86 formed on the neck portion 62 of the cylinder 22. Because the tabs 86 and slots 88 are placed at unequal intervals, only one orientation of the cap 24 relative to the cylinder 22 will properly align the tabs 86 within the slots 88, minimizing accidental locking. Those skilled in the art will further recognize that other mating surface structures besides the tabs 86 and slots 88 described could also be used to properly align the cap 24 relative to the cylinder 22. After alignment, when the cap 24 and cylinder 22 are pushed together, the ridges 82 in the inside wall 84 engage the mating ridges 80 formed on the cylinder 22, thus creating a snap fit of the cap 24 onto the proximal end 64 of the cylinder 22. As described above, both sets of ridges 80, 82 are preferably formed of medical grade Lexan, however, other materials which are somewhat flexible to permit the ridges 80, 82 to bend and then snap back, thereby creating the snap fit to lock the cap 24 onto the cylinder 22, could also be used. Thus, the cap 24 of the present invention prohibits contact with the needle 58 and/or use of the needle 58 after the syringe is disposed of. In addition, the width of the cap 24 at the mouth 66 advantageously minimizes the risk of inadvertent contact with the needle 58 as the cap 24 is placed on the syringe, protecting medical personnel from contaminated blood which may be carried on the needle 58. Once the cap 24 is placed on the cylinder 22, the syringe can then be safely disposed of without the possibility of re-use in unsanitary conditions.

Alternatively, the needle 58 may be initially provided within the cap 24 prior to syringe use, such that the cap 24 is then used to attach the needle 58 to the syringe, while the cap can be supplied as a separate element. The needle 58 may be detachably held within the cap 24 in any well known manner such as, for example, with plastic tacking which is broken by twisting and/or pulling on the cap 24 after the needle 58 has been twisted onto the threads 60 in the cylinder neck 62. In this manner, the sharp end of the needle 58 is enclosed within the cap 24 while the needle 58 is screwed onto the internal threads 60 within the neck region 62 of the cylinder 22 to further prevent accidental needle contact. As long as the slots 88 in the cap 24 are not aligned with the tabs 86 on the cylinder 22 and no force is applied to push the cap onto the cylinder, the cap can be easily pulled off once the needle 58 has been screwed onto the syringe cylinder 22 and the syringe is then used to give an injection is the manner previously described. When the injection has been administered, the alignment tabs 86 on the cylinder 22 are aligned with the slots 88 in the cap 24 and the cap is then pushed onto the cylinder to engage the annular ridges 82 inside the cap with the mating ridges 80 on the cylinder 22, thereby locking the cap 24 onto the needle 58 such that the needle is covered and the syringe can then be safely disposed of. Again, the placement of the tabs 86 and slots 88 allows only one orientation of the cap 24 relative to the cylinder 22 to lock the cap over the needle 58, thus preventing accidental locking.

Figure 13:
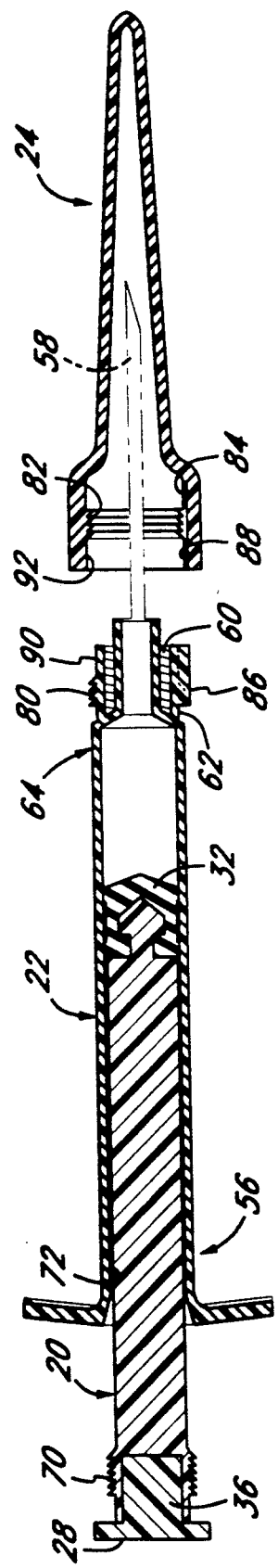
FIG. 13 is a side cross-sectional view illustrating a further embodiment of the invention.

In a further embodiment of the invention illustrated in FIG. 13, the cylinder 22 and cap 24 include non-ridged regions 90, 92 formed adjacent the ridges 80, 82, respectively. Preferably, the needle is supplied already attached to the cylinder 22 and packaged in this manner. The syringe 10 is further preferably packaged such that the cap 24 covers the needle 58. The cap 24 is placed on the proximal end 64 of the cylinder 22 such that the ridges 80 on the proximal end 64 of the cylinder are covered by the non-ridged region 92 along the inner wall 84 of the cap. In this position, the annular ridges 80 on the cylinder 22 abut the annular ridges 82 in the cap 24, such that the cap fits snugly onto the cylinder to cover the needle 58 but is not locked thereon. In this configuration, the cap 24 advantageously reduces the risk of needle contact during removal of the syringe 10 from packaging and during preparation of an injection. Prior to administering the injection, the cap 24 is removed from the cylinder 22 with a pulling force. The injection is then administered and the cap 24 locked onto the cylinder 22 in the manner described above prior to disposal of the syringe 10.

Figure 14:
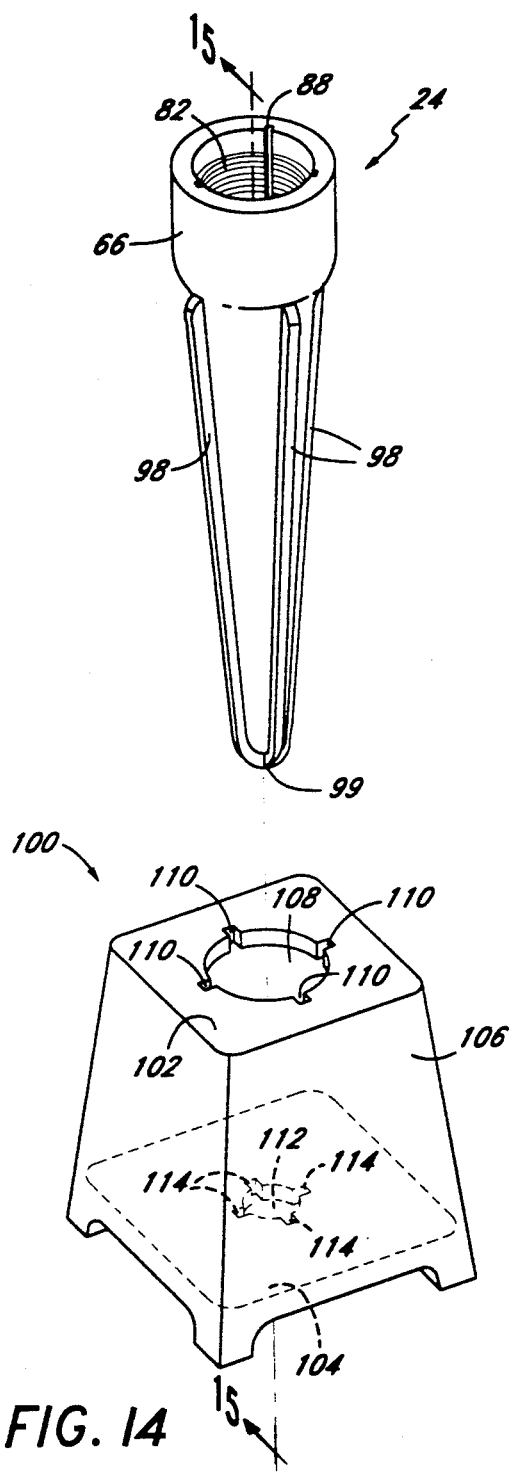
FIG. 14 is a perspective view illustrating another embodiment of the syringe cap and a cap holder.

In yet another aspect of the invention illustrated in FIG. 14, the cap 24 may include a plurality of alignment structures. Preferably, the alignment structures comprise exterior longitudinal ridges 98 which originate adjacent the mouth portion 66 and extend along the length of the cap terminating at the tip 99 of the cap 24. The cap 24 may be attached to the syringe cylinder 22 utilizing a cap holder 100. The holder 100 is generally rectangular and includes a top surface 102, a bottom surface 104, and side walls 106 which are angled slightly with respect to the top and bottom surfaces. The top surface 102 includes a first opening 108 having a plurality of alignment structures 110 formed in the perimeter thereof. The opening 108 is preferably circular and the alignment structures 110 preferably comprise notches which are formed in the circumference of the circular opening. The bottom surface 104 includes a second opening 112 which is smaller than that of the first opening 108 in the top surface 102 of the holder 100. The opening 112 in the bottom surface 104 also includes a plurality of alignment structures 114 formed in the perimeter thereof. The opening 112 is preferably circular and the alignment structures 114 preferably comprise notches formed in the circumference of the circular opening. The interior of the holder 102 is hollow.

Figure 15:
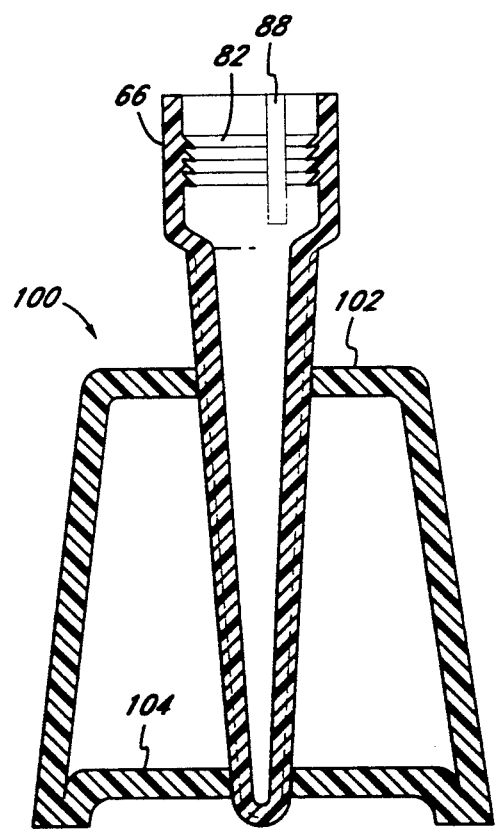
FIG. 15 is a cross-sectional view of the cap positioned within the holder taken along lines 15—15 of FIG. 14.

When an injection has been given, the cap 24 may be placed on the syringe using the holder 100. The holder 100 can be mounted to a counter top, wall, or other suitable surface in a clinical environment. Further, although a preferred configuration of the holder 100 has been illustrated, those skilled in the art will recognize that the holder could have various configuration and could be as simple as a hole formed in a counter top. To position the cap 24 within the holder 100, the longitudinal alignment ridges 98 on the exterior of the cap 24 are aligned with the corresponding alignment notches 110 in the opening 108 in the top surface 102 and the cap is inserted downward through the circular opening 108 into the hollow interior of the holder. The longitudinal ridges 98 remain aligned with the alignment notches 110 and the cap 24 is further inserted until the ridges 98 are inserted through the corresponding alignment notches 114 in the opening 112 in the bottom surface 104 of the holder 100 and the tip 99 of the cap rests within the opening 112, as shown in FIG. 15.

Once the cap 24 has been fixed within the holder 100 in this manner, the cap may be attached to the cylinder 22 after an injection has been given by inserting the cylinder and needle 58 carried thereon into the mouth portion 66 of the cap. The tabs 86 formed on the neck portion 62 of the cylinder 22 are then aligned with the slots 88 in the interior wall of the cap 24. The holder 100 advantageously enables the cylinder to be turned or twisted while the cap 24 remains in a fixed position during this alignment process. The exterior ridges 98 on the cap 24 can also be oriented opposite the slots 88 in the interior of the cap to facilitate alignment of the cylinder 22 within the cap 24. After alignment, a pushing force is applied and the ridges 82 on the inside wall of the cap 24 engage the mating ridges 80 formed on the cylinder, thereby locking the cap onto the cylinder and prohibiting re-use of the needle 58. The syringe is then removed from the holder 100 by applying a pulling force to the cylinder 22 to remove the cylinder and cap 24 locked thereon from the holder 100. Thus, it will be appreciated by those skilled in the art that the holder facilitates placement of the cap 24 on the syringe cylinder 22 while further minimizing accidental needle contact during this process.

Although the invention has been described with reference to specific embodiments, the description is intended to be illustrative of the invention and is not intended to be limiting. Various modifications and applications may occur to those skilled in the art without departing from the true spirit and scope of the invention defined in the appended claims.

What is claimed is:

1. A locking syringe, comprising:
   a cylinder having an open, cylindrical passage, said cylinder including a distal end having a first plunger locking member, and a proximal end adapted to hold a needle, said proximal end of said cylinder including a first cap locking member;
   a plunger comprising a shaft having a proximal end and a distal end wherein said distal end includes a second plunger locking member, said second plunger locking member comprising a second set of annular ridges, said second plunger locking member is matable with said first plunger locking member on said cylinder when said plunger is inserted in said cylinder, thereby prohibiting removal of said plunger from said cylinder;
   said first plunger locking member comprising a first set of annular ridges which further include a plurality of channels formed therethrough to facilitate insertion of a plunger into said cylinder;
   a cap having a wide opening and a length sized to cover a needle which may be carried on said cylinder, said cap including a second cap locking member which engages said first cap locking member on said proximal end of said cylinder, thereby preventing reuse of said needle carried on said cylinder.

2. A locking syringe, comprising:
   a cylinder having an open, cylindrical passage, said cylinder including a distal end having a first plunger locking member and a proximal end adapted to hold a needle and having a first cap locking member, said first cap locking member comprising a first set of annular ridges;
   a plunger comprising a shaft having a proximal end and a distal end wherein said distal end includes a second plunger locking member which is matable with said first plunger locking member on said cylinder when said plunger is inserted in said cylinder, thereby prohibiting removal of said plunger from said cylinder; and
   a cap having a wide opening and a length sized to cover a needle which may be carried on said cylinder, said cap including a second cap locking member, comprising a second set of annular ridges which engages said first cap locking member on said proximal end of said cylinder, thereby preventing reuse of said needle carried on said cylinder;
   wherein one of said two cap locking members further includes a plurality of tabs formed thereon and the other of said cap locking members further includes a plurality of slots formed 3. A syringe comprising:
   a plunger having a first locking member formed at the distal end thereof, said first locking member comprising a set of annular ridges;
   a cylinder having a proximal end adapted to hold a needle and a distal end having a second locking member adjacent thereto, said second locking member comprising a second set of annular ridges having a plurality of longitudinal channels formed therethrough to facilitate insertion of said plunger into said cylinder, and said first locking member matable with said second locking member when said plunger is fully inserted into said cylinder to lock said plunger in said cylinder, thereby preventing reuse of said syringe.

4. A locking syringe, comprising:
   a syringe body having:
      a distal end,
      an open cylindrical passage,
      a first plunger locking member located only adjacent the distal end of said cylindrical passage, said first plunger locking member comprising a set of annular ridges having a plurality of channels formed therethrough, and
      a proximal end adapted to hold a needle and having a first cap locking member, said cylindrical passage being otherwise free of locking members;
   a plunger comprising a shaft having a proximal end and a distal end, and a second plunger locking member comprising a set of annular ridges located only adjacent the distal end of said shaft, which second plunger locking member is matable with said first plunger locking member on said cylinder when said plunger is inserted in said cylinder, thereby prohibiting removal of said plunger from said cylinder, said plunger being otherwise free of locking members;
   a thrust plate affixed to the distal end of said shaft beyond the second plunger locking member, said thrust plate being of sufficient size to extend laterally beyond the perimeter of the distal end of said cylindrical passage such that when said plunger is fully inserted into said syringe body, said thrust plate is located outside of said syringe body; and
   a longitudinally tapered cap having a wide opening at one end thereof and a length sized to cover a needle which may be carried on said cylinder, said cap including a second cap locking member which engages said first cap locking member on said proximal end or said cylinder, thereby preventing reuse of said needle carried on said cylinder.

5. A locking syringe, comprising:
   a syringe body having a distal end, an open cylindrical passage, a first plunger locking member located only adjacent the distal end of said cylindrical passage, and a proximal end adapted to hold a needle and having a first cap locking member, said first cap locking member comprising a set of annular ridges, said cylindrical passage being otherwise free of locking members;
   a plunger comprising a shaft having a proximal end and a distal end, and a second plunger locking member located only adjacent the distal end of said shaft, which second plunger locking member is matable with said first plunger locking member on said cylinder when said plunger is inserted in said cylinder, thereby prohibiting removal of said plunger from said cylinder, said plunger being otherwise free of locking members;

a thrust plate affixed to the distal end of said shaft beyond the second plunger locking member, said thrust plate being of sufficient size to extend laterally beyond the perimeter of the distal end of said cylindrical passage such that when said plunger is fully inserted into said syringe body, said thrust plate is located outside of said syringe body;

a longitudinally tapered cap having a wide opening at one end thereof and a length sized to cover a needle which may be carried on said cylinder, said cap including a second cap locking member which engages said first cap locking member on said proximal end of said cylinder, thereby preventing reuse of said needle carried on said cylinder;

a plurality of tabs formed on one of said two cap locking members; and a plurality of slots formed in the other of said two cap locking members, wherein said slots may be aligned with said tabs to lock said cap onto said cylinder.

6. The locking syringe defined in claim 5, wherein said tabs and slots are formed at unequal intervals around the circumference of said annular ridges.

7. A method for administering an injection of a fluid using a syringe, said method comprising the steps of:

providing a syringe plunger having a first lock element located only at its distal end;

providing a syringe body having proximal and distal ends, a cylindrical passage, and a second lock element, located only adjacent the distal end of said cylindrical passage, which mates whit said first lock element;

providing a thrust plate, affixed at the distal end of said plunger, said thrust plate being of sufficient size to extend laterally beyond the perimeter of the distal end of said cylindrical passage;

depressing said plunger into said cylindrical passage of said syringe body to eject said fluid from said syringe body, thereby bringing said thrust plate closer to, but still outside of said distal end of said syringe body, and engaging said first lock element on said plunger with said second lock element in said cylindrical passage to prevent removal of said plunger from said cylindrical passage;

providing a cap having a third lock element which mates with a fourth lock element on said cylinder; and positioning said cap on said cylinder, and aligning said third lock element with said fourth lock element, such that said third lock element mates with said fourth lock element to lock said cap onto said cylinder.

8. A method for administering an injection of a fluid using a syringe, said method comprising the steps of:

providing a syringe plunger having a first lock element located only at its distal end;

providing a syringe body having proximal and distal ends, a cylindrical passage, and a second lock element, located only adjacent the distal end of said cylindrical passage, which mates whit said first lock element;

providing a thrust plate, affixed at the distal end of said plunger, said thrust plate being of sufficient size to extend laterally beyond the perimeter of the distal end of said cylindrical passage;

depressing said plunger into said cylindrical passage of said syringe body to eject said fluid from said syringe body, thereby bringing said thrust plate closer to, but still outside of said distal end of said syringe body, and engaging said first lock element on said plunger with said second lock element in said cylindrical passage to prevent removal of said plunger from said cylindrical passage;

providing a cap having a third lock element which mates with a fourth lock element on said cylinder;

placing said cap within a cap holder such that said cap is fixedly held by said holder;

positioning said cylinder within said cap such that said third locking element is aligned with said fourth lock element; and engaging said third lock element with said fourth lock element such that said cap locks onto said cylinder.

9. A locking syringe, comprising:

a syringe body having a distal end, an open cylindrical passage, a first plunger locking member located only adjacent the distal end of said cylindrical passage, a proximal end adapted to hold a needle and having a first cap locking member, said first cap locking member comprising a set of annular ridges, and a non-ridged region adjacent said first cap locking member, said cylindrical passage being otherwise free of locking members;

a plunger comprising a shaft having a proximal end and a distal end, and a second plunger locking member located only adjacent the distal end of said shaft, which second plunger locking member is matable with said first plunger locking member on said cylinder when said plunger is inserted in said cylinder, thereby prohibiting removal of said plunger from said cylinder, said plunger being otherwise free of locking members;

a thrust plate affixed to the distal end of said shaft beyond the second plunger locking member, said thrust plate being of sufficient size to extend laterally beyond the perimeter of the distal end of said cylindrical passage such that when said plunger is fully inserted into said syringe body, said thrust plate is located outside of said syringe body; and a longitudinally tapered cap having a wide opening at one end thereof and a length sized to cover a needle which may be carried on said cylinder, said cap including a second cap locking member comprising a set of annular ridges, and a non-ridged region adjacent said second cap locking member, wherein said second cap locking member engages said first cap locking member on said proximal end of said cylinder, thereby preventing reuse of said needle carried on said cylinder.

10. A locking syringe, comprising:

a cylinder having an open, cylindrical passage, said cylinder including a distal end having a first plunger locking member and a proximal end adapted to hold a needle and having a first cap locking member, said first cap locking member comprising a first set of annular ridges;

a plunger comprising a shaft having a proximal end and a distal end wherein said distal end includes a second plunger locking member which is matable with said first plunger locking member o said cylinder when said plunger is inserted in said cylinder, thereby prohibiting removal of said plunger from said cylinder; and a cap having a wide opening and a length sized to cover a needle which may be carried on said cylinder, said cap including a second cap locking member, comprising a second set of annular ridges which engages said first cap locking member on said proximal end of said cylinder, thereby preventing reuse of said needle carried on said cylinder;

wherein one of said two cap locking members further includes a plurality of tabs formed thereon and the other of said cap locking members further includes a plurality of slots formed therein, said tabs and slots being formed at unequal intervals around the circumference of said annular ridges, wherein said slots may be aligned with said tabs to further secure said cap onto said cylinder.

* * * * *

UNITED STATES PATENT AND TRADEMARK OFFICE
CERTIFICATE OF CORRECTION

PATENT NO. : 5,259,840
DATED : November 9, 1993
INVENTOR(S) : Craig R. Boris

It is certified that error appears in the above-indentified patent and that said Letters Patent is hereby corrected as shown below:

Column 7, line 68, change "slots formed" to --slots formed therein, wherein said slots may be aligned with said tabs to further secure said cap onto said cylinder.--

Column 9, Line 34, change "which mates whit" to --which mates with--

Column 9, Line 63, change "which mates whit" to --which mates with--

Signed and Sealed this

Tenth Day of June, 1997

BRUCE LEHMAN

Attest:

Attesting Officer

Commissioner of Patents and Trademarks